United States Patent [19]
Yarborough

[11] Patent Number: 5,645,428
[45] Date of Patent: Jul. 8, 1997

[54] METHOD FOR WHITENING TEETH

[75] Inventor: David K. Yarborough, Birmingham, Ala.

[73] Assignee: BriteSmile, Inc., Salt Lake City, Utah

[21] Appl. No.: 570,901

[22] Filed: Dec. 12, 1995

[51] Int. Cl.$^6$ .............................. A61K 6/00; A61K 33/10; A61K 33/08; A61K 7/20
[52] U.S. Cl. .............................. 433/215; 514/714; 424/687; 424/688; 424/693; 424/710; 424/709; 424/717
[58] Field of Search .................... 514/714; 424/687, 424/688, 693, 710, 717, 709; 433/215

[56] References Cited

U.S. PATENT DOCUMENTS

| | | | |
|---|---|---|---|
| 4,582,701 | 4/1986 | Piechota | 424/52 |
| 4,661,070 | 4/1987 | Friedman | 433/203.1 |
| 4,687,663 | 8/1987 | Schaeffer | 424/52 |
| 4,877,401 | 10/1989 | Higuchi et al. | 433/215 |
| 4,983,380 | 1/1991 | Yarborough | 424/52 |
| 4,983,381 | 1/1991 | Torres Zaragoza | 424/53 |
| 5,009,885 | 4/1991 | Yarborough | 424/53 |
| 5,032,178 | 7/1991 | Cornell | 106/35 |
| 5,041,280 | 8/1991 | Smigel | 424/52 |
| 5,123,845 | 6/1992 | Vassiliadis et al. | 433/215 |
| 5,306,143 | 4/1994 | Levy | 433/29 |
| 5,318,562 | 6/1994 | Levy et al. | 606/16 |
| 5,409,631 | 4/1995 | Fischer | 252/186.25 |

FOREIGN PATENT DOCUMENTS

| | | |
|---|---|---|
| 8307091 | 10/1983 | Spain . |
| 528007 | 9/1985 | Spain . |

OTHER PUBLICATIONS

Journal of Endodontics, vol. 15, No. 3, Mar. 1989, Stewart Ho, DMD and Albert C. Goerig, DDS, MS, FICD "An In Vitro Comparison of Different Bleaching Agents in the Discolored Tooth".

Asian Journal of Aesthetic Dentistry, vol. 1, No. 2 Jul. 1993, C.G. Toh "Clinical evaluation of a dual–activated bleaching system".

*Primary Examiner*—Phyllis G. Spivack
*Attorney, Agent, or Firm*—Weil, Gotshal & Manges LLP

[57] ABSTRACT

A method for whitening teeth which utilizes laser light to activate bleaching agents applied to the teeth. The mouth is first prepared so that the soft tissues of the gums are protected and only the teeth are exposed. The teeth are cleaned to remove any materials which will reduce or nullify the effects of the bleaching agents. A mixture of peroxide and a first catalyst are prepared and applied to the teeth. The teeth are exposed to laser light from an argon laser which light activates the peroxide and catalyst to accelerate the bleaching process without heat. Next, a mixture of peroxide and a second catalyst are prepared and applied to the teeth. The teeth are briefly exposed to laser light from a carbon dioxide laser which heat activates the peroxide and catalyst to accelerate the bleaching process.

37 Claims, No Drawings

METHOD FOR WHITENING TEETH

FIELD OF THE INVENTION

The present invention relates to a method for whitening teeth. More particularly, the present invention relates to a method for whitening teeth which utilizes laser light to activate bleaching agents.

BACKGROUND OF THE INVENTION

Development in the field of teeth whitening has led to the present method of "power bleaching". The method begins with placing a rubber sheet or dam over the patient's teeth and pushing the teeth through the sheet. This protects the soft tissues of the gums from oxidation by peroxides used in bleaching. However, since the rubber sheet stretches and does not custom fit the particular patient's mouth, the peroxide can leak around the rubber sheet and cause substantial discomfort to the patient. Typically, this method can be performed only on the upper or lower set of teeth at one time, not both.

Once the rubber sheet is in place, a peroxide solution is coated on the teeth. Since the bleaching effects of peroxide are slow, the common practice is to apply heat to the peroxide to accelerate the reaction. This is accomplished with the use of a heat lamp or heating iron. Although the heat accelerates the bleaching process, a substantial amount of time is still required so that the entire bleaching process must be performed over several appointments, resulting in inconvenience, time loss, and substantial expense.

The heat lamp activates the peroxide on a plurality of teeth simultaneously but also exposes the patient's face to the heat, which is quite uncomfortable and cannot be endured for a prolonged period. While the heating iron does not expose the patient's face to the same extent as the heat lamp, it takes a much longer time to perform the whitening since it affects only one or two teeth at a time. In addition, prolonged exposure to heat will increase the temperature of the pulp within the tooth. Since the amount of heat commonly used in this type of procedure could kill the pulp and cause tooth loss if exposure is prolonged, continuous exposure must be limited. As a result, 2 to 5 office visits are required before adequate bleaching is attained. From the foregoing it maybe seen that there is still a need for a method of whitening teeth which better protects the soft tissues, shortens the time for the procedure, and reduces the discomfort to the patient.

SUMMARY OF THE PRESENT INVENTION

It is the object of the present invention to provide a method for whitening teeth which substantially reduces discomfort to the patient.

It is another object of the present invention to provide a method which can be performed within a short period of time, requiring only one office visit.

These and other objects of the present invention are accomplished through a method which utilizes laser light to activate bleaching agents applied to the teeth. The mouth is first prepared so that the soft tissues of the gums are protected and only the teeth are exposed. The teeth are cleaned to remove any materials which will reduce or nullify the effects of the bleaching agents. A mixture of peroxide and a first catalyst are prepared and applied to the teeth. The teeth are exposed to laser light from an argon laser which light activates the peroxide and catalyst to accelerate the bleaching process without heat. Next, a mixture of peroxide and a second catalyst are prepared and applied to the teeth. The teeth are briefly exposed to laser light from a carbon dioxide laser which heat activates the peroxide and catalyst to accelerate the bleaching process.

These and other objects and advantages of the invention will become apparent from the following detailed description of the preferred method.

DETAILED DESCRIPTION OF THE PREFERRED EMBODIMENT

Whitening teeth can be achieved dramatically and quickly using laser energy to activate a peroxide and catalyst solution which has been applied to the patient's teeth. This method of whitening teeth, according to the preferred embodiment, can be performed in one office visit and subjects the patient to minimal discomfort. The method begins with isolating the patient's teeth so that only the teeth are exposed and the gums are protected. First, strips of a wax-like material having an adhesive quality are applied over the patient's upper and lower gums such that one side of each strip overlays the part of the teeth adjacent the gums. This side of each strip is molded so that it follows the contour of the gums adjacent the teeth, a process called "scalloping". Any remaining exposed soft tissues of the cheeks or gums are protected with substances which will break down peroxides, such as non-toxic metallic or enzymatic solutions created for this purpose.

The next step is cleaning the front surfaces of the teeth to remove any deposits which can interfere with the bleaching process, such as iron residues in lipstick, calculus, or plaque. The preferred cleaning solution contains: approximately 50% purified ethanol, although any concentration between 30% and 90% can be used; approximately 10% hydrogen peroxide, although any concentration between 0% and 30% can be used; an acid selected from the group consisting of phosphoric, citric, hydrochloric, acetic, and hydrofluoric acids; and deionized distilled water. Typically, the final concentration of acid is approximately 10%, although any concentration between 3% and 35% can be used. After cleaning, the teeth are rinsed with deionized distilled water so that no significant contaminants remain on the front surfaces of the teeth.

The next step is preparing and applying a first bleaching mixture on the patient's teeth. The preferred bleaching mixture contains an oxygen radical generating agent such as a peroxide, an oxygen radical releasing agent such as a catalyst, a desensitizing and color stabilizing agent, a thickening agent, and a buffer for maintaining a desired pH range. The preferred peroxide is hydrogen peroxide, although any peroxide selected from the group consisting of hydrogen peroxide, carbamide peroxide, calcium bicarbonate peroxide, sodium bicarbonate peroxide, or any other oxygen radical generating agents. The preferred concentration of hydrogen peroxide in the mixture is approximately 50%, although any concentration between 3% and 90% can be used. The catalyst is selected from the group consisting of ammonium persulfate and potassium persulfate and has a final concentration of 30%, although concentrations between 1% and 80% are effective. The desensitizing and color stabilizing agent is selected from the group consisting of fluoride, calcium, and phosphate, and is used at a final concentration of 1% for fluoride, 5% for calcium, or 2% for phosphorus, although a concentration between 0.1% and 10% can be used for any of these substances. The thickening agent is selected from the group consisting of silicates, cellulose compounds such as hydroxyethylcellulose, lanolate, palmitate, oleate, sodium lauryl sulfate, sodium stearate, calcium stearate, and other fatty acids. Typically, the thickening agents are used at a final concentration of 5%, although any concentration between 1% and 20% can be used. The buffer is selected from the group consisting of urea, sodium carbonate, sodium bicarbonate, calcium carbonate, calcium bicarbonate, sodium hydroxide, potassium hydroxide and calcium hydroxide, although any buffering agent can be used. The concentration of the buffer will depend on what is necessary to maintain a pH between 7 and 11, although the optimal pH is between 7.8 and 10.5. Once mixed, a 1 to 2 millimeter layer of the bleaching mixture is applied to the front surface of the patient's teeth.

The next step is light activating the first bleaching mixture with light from an argon laser. The argon laser is the preferred light source although a nitrogen or excimer ultraviolet laser can also be used. The argon laser has a power output between 0.35 to 4.0 watts with an optimal range between 0.85 to 2.0 watts, a wavelength range between 488 and 510 nanometers, although a range between 300 and 520 nanometers can be used, and a beam diameter between 0.1 to 8.0 millimeters. Each tooth is exposed for approximately 30 seconds but may be exposed for approximately 1 to 60 seconds. Once all teeth have been treated, remaining bleaching mixture is removed from the teeth. If needed, the previous steps of applying the bleaching mixture and activating with the argon laser can be repeated.

The next step is preparing and applying a second bleaching mixture on the patient's teeth. The preferred bleaching mixture contains an oxygen radical generating agent such as a peroxide, an oxygen radical releasing agent such as a catalyst, a a desensitizing and color stabilizing agent, a thickening agent, and a buffer for maintaining a desired pH range. The peroxide, the a desensitizing and color stabilizing agent, the thickening agent, and the buffer and pH range are the same as the first bleaching mixture. The catalyst is selected from the group consisting of sodium perborate, sodium carbonate, sodium bicarbonate, sodium hydroxide, potassium hydroxide, calcium carbonate, and calcium hydroxide. Typically, the catalyst is used at a final concentration of 30%, although any concentration between 3% and 80% can be used. Once mixed, a 1 to 2 millimeter layer of the bleaching mixture is applied to the front surface of the patient's teeth.

Some of the foregoing catalysts, such as sodium carbonate and sodium bicarbonate, are also used as buffers. The reason for their additional inclusion as a catalyst is due to their hydrophilic affect. A catalyst is any substance that causes a change in the rate of a chemical reaction without itself being consumed by the reaction. In water, ions are surrounded by a layer of water molecules, called a primary hydration sphere. As the water molecules form this primary sphere around the ions, their polarity is oriented to exert an enhanced hydrogen-bonding attraction on other water molecules. This results in formation of a secondary hydration layer around the first layer. Subsequent hydration layers can also form, depending on the size and charge of the ions. As water molecules are pulled into these hydration layers, the effective concentration of the oxygen radical generating agent is increased, resulting in greater instability and a faster rate of reaction.

The next step is heat activating the second bleaching mixture with light from a carbon dioxide laser, although any other short or long wave infrared laser can be used. The only other infrared laser presently approved for use by the Federal Drug Administration is the Yttrium Arsenic Gallium (YAG) laser, however this has detrimental side effects and is not the preferred laser for this step. The carbon dioxide laser is very safe because it interacts directly with the water molecules on the surface of the teeth and only penetrates approximately 0.1 millimeter into the aqueous coating. The carbon dioxide laser has a power output between 0.5 to 50 watts, a wavelength between 10 and 11 micrometers, and a beam diameter between 1 to 3 millimeters. Each tooth is exposed from 0.1 millisecond pulses to continuous exposure for a total exposure time between 1 to 10 seconds to prevent overheating of the enamel. Once all teeth have been treated, remaining bleaching mixture is removed from the teeth. If needed, the previous steps of applying the bleaching mixture and activating with the carbon dioxide laser can be repeated.

It is to be understood that the method of the invention disclosed is a preferred embodiment thereof and that various changes and modifications may be made therein without departing from the spirit of the invention or scope as defined in the following claims.

Having set forth the nature of the invention, what is claimed is:

1. A method for whitening a patient's teeth comprising the steps of:
    (a) preparing a mixture comprising an oxygen radical generating agent and an oxygen radical releasing agent;
    (b) applying said mixture to said patient's teeth; and
    (c) exposing said patient's teeth to laser light for a selected interval to accelerate whitening, wherein said preparing step includes selecting said oxygen radical generating agent from the peroxide group consisting of hydrogen peroxide, carbamide peroxide, calcium bicarbonate peroxide, and sodium bicarbonate peroxide.

2. A method as described in claim 1, wherein said preparing step includes providing a concentration of said oxygen radical generating agent in said mixture between 3% and 90%.

3. A method as described in claim 2, wherein said oxygen radical releasing agent is selected from the group consisting of sodium carbonate, sodium bicarbonate, calcium carbonate, calcium hydroxide, ammonium persulfate, potassium persulfate, and sodium perborate.

4. A method as described in claim 3, wherein said preparing step includes providing a concentration of said oxygen radical releasing agent in said mixture between 3% and 80%.

5. A method as described in claim 3, wherein said exposure step utilizes said laser light from a carbon dioxide laser with a wavelength in the infrared spectrum and a power output of at least 500 milliwatts.

6. A method as described in claim 1, wherein said exposure step utilizes said laser light from an argon laser with a wavelength range between approximately 400 and 520 nanometers and a power output of at least 350 milliwatts.

7. A method as described in claim 1, wherein said exposing step comprises exposing said teeth to light from an argon laser.

8. A method as described in claim 1, wherein said exposing step comprises exposing said teeth to light from a carbon dioxide laser.

9. A method for whitening a patient's teeth comprising the steps of:
    (a) preparing a mixture comprising an oxygen radical generating agent and an oxygen radical releasing agent:
    (b) applying said mixture to said patient's teeth: and
    (c) exposing said patient's teeth to laser light for selected interval to accelerate whitening, wherein said oxygen radical releasing agent is selected from the group consisting of sodium carbonate, sodium bicarbonate, calcium carbonate, calcium hydroxide, ammonium persulfate, potassium persulfate, and sodium perborate.

10. A method as described in claim 9, wherein said preparing step includes providing a concentration of said oxygen radical releasing agent in said mixture between 3% and 80%.

11. A method for whitening a patient's teeth comprising the steps of:
   (a) preparing a mixture comprising an oxygen radical generating agent and an oxygen radical releasing agent;
   (b) applying said mixture to said patient's teeth; and
   (c) exposing said patient's teeth to laser light for a selected interval to accelerate whitening,
wherein said preparing step further comprises preparing said mixture with:
   (i) a buffer selected from the group consisting of urea, sodium carbonate, sodium bicarbonate, calcium carbonate, calcium bicarbonate, calcium hydroxide, or any other buffering agent to maintain a pH of said mixture between 7 and 11;
   (ii) a desensitizing and color stabilizing agent selected from the group consisting of fluoride, calcium, and phosphate and providing a concentration of said desensitizing and color stabilizing agent in said mixture between 0.1% and 10%; and
   (iii) a thickening agent selected from the group consisting of silicates, hydroxyethylcellulose, lanolate, palmitate, oleate, sodium lauryl sulfate, sodium stearate, calcium stearate, and other fatty acids and providing a concentration of said thickening agent in said mixture between 1% and 20% .

12. A method for whitening a patient's teeth comprising the steps of:
   (a) preparing a mixture comprising an oxygen radical generating agent and an oxygen radical releasing agent:
   (b) applying said mixture to said patient's teeth; and
   (c) exposing said patient's teeth to laser light for a selected interval to accelerate whitening, wherein said exposure step utilizes laser light from an argon laser with a wavelength range between approximately 300 and 520 nanometers and a power output of at least 350 milliwatts.

13. A method as described in claim 12, wherein said exposure step includes a total exposure time from said argon laser between approximately 1 and 60 seconds per tooth.

14. A method as described in claim 13, wherein said exposure step further utilizes laser light from a carbon dioxide laser with a wavelength in the infrared spectrum and a power output of at least 500 milliwatts.

15. A method as described in claim 14, wherein said wavelength of said carbon dioxide laser is between approximately 10 and 11 micrometers.

16. A method as described in claim 15, wherein said exposure step utilizes 0.1 millisecond pulses to continuous exposure from said carbon dioxide laser for a total exposure time between approximately 1 and 10 seconds per tooth.

17. A method for whitening a patients's teeth comprising the steps of:
   (a) preparing a mixture comprising an oxygen radical generating agent and an oxygen radical releasing agent;
   (b) applying said mixture to said patient's teeth; and
   (c) exposing said patient's teeth to laser light for a selected interval to accelerate whitening, wherein said exposure step utilizes laser light from a carbon dioxide laser with a wavelength in the infrared spectrum and a power output of at least 500 milliwatts.

18. A method as described in claim 17, wherein said wavelength of said carbon dioxide laser is between approximately 10 and 11 micrometers.

19. A method as described in claim 18, wherein said exposure step utilizes 0.1 millisecond pulses to continuous exposure from said carbon dioxide laser for a total exposure time between approximately 1 and 10 seconds per tooth.

20. A method for whitening a patient's teeth comprising the steps of:
   (a) isolating the patient's teeth so that only the teeth are exposed;
   (b) cleaning the surface of the teeth to remove any agents which will inhibit an oxygen radical generating agent;
   (c) treating any exposed soft tissues with a tissue protectant;
   (d) mixing a first mixture comprising an oxygen radical generating agent and a first oxygen radical releasing agent;
   (e) applying said first mixture to said patient's teeth;
   (f) exposing said patient's teeth to fight from an argon laser;
   (g) mixing a second mixture comprising said oxygen radical generating agent and a second oxygen radical releasing agent;
   (h) applying said second mixture to said patient's teeth; and
   (j) exposing said patient's teeth to light from a carbon dioxide laser.

21. A method as described in claim 20, wherein said isolating step in (a) includes:
   (a) applying strips of a wax-like material with an adhesive quality over the patient's gums; and
   (b) molding said strips so that they follow the contour of said gums with said teeth.

22. A method as described in claim 20, wherein said mixing step in (d) includes selecting said oxygen radical generating agent from the peroxide group consisting of hydrogen peroxide, carbamide peroxide, calcium bicarbonate peroxide, and sodium bicarbonate peroxide, or any other oxygen radical generating agents.

23. A method as described in claim 22, wherein said mixing step in (d) includes providing a concentration of said oxygen radical generating agent in said first mixture between 3% and 90%.

24. A method as described in claim 20, wherein said mixing step in (d) includes selecting said first oxygen radical releasing agent from the group consisting of ammonium persulfate and potassium persulfate.

25. A method as described in claim 24, wherein said mixing step in (d) includes providing a concentration of said first oxygen radical releasing agent in said first mixture between 1% and 80%.

26. A method as described in claim 20, wherein said mixing step in (d) further comprises preparing said first mixture with:
   (a) a buffer selected from the group consisting of urea, sodium carbonate, sodium bicarbonate, sodium hydroxide, potassium hydroxide, calcium carbonate, calcium bicarbonate, calcium hydroxide, or any other buffering agent to maintain a pH of said first mixture between 7 and 11;
   (b) a a desensitizing and color stabilizing selected from the group consisting of fluoride, calcium, and phosphate; and (c) a thickening agent selected from the group consisting of silicates, hydroxyethylcellulose, lanolate, palmitate, oleate, sodium lauryl sulfate, sodium stearate, calcium stearate, and other fatty acids.

27. A method as described in claim 20, wherein said mixing step in (g) includes selecting said oxygen radical releasing agent from the group consisting of sodium carbonate, sodium bicarbonate, sodium hydroxide, potassium hydroxide, calcium carbonate, calcium hydroxide, and sodium perborate.

28. A method as described in claim 27, wherein said mixing step in (g) includes providing a concentration of said second oxygen radical releasing agent between 3% and 80%.

29. A method as described in claim 20, wherein said exposure step in (f) utilizes said argon laser light having a wavelength range between approximately 400 and 520 nanometers and a power output of at least 350 milliwatts.

30. A method as described in claim 29, wherein said exposure step in (f) includes an exposure time from said argon laser between approximately 1 and 60 seconds per tooth.

31. A method as described in claim 20, wherein said exposure step in (j) utilizes said carbon dioxide laser light having a wavelength in the infrared spectrum and a power output of at least 500 milliwatts.

32. A method as described in claim 30, wherein said wavelength of said carbon dioxide laser is between approximately 10 and 11 micrometers.

33. A method as described in claim 31, wherein said exposure step in 6) utilizes 0.1 millisecond pulses to continuous exposure from said carbon dioxide laser for a total exposure time between approximately 1 and 10 seconds per tooth.

34. A composition for use in whitening teeth when subjected to laser light comprising:

(a) a primary composition for use in a first phase of whitening comprising an oxygen radical generating agent selected from the peroxide group consisting of hydrogen peroxide, carbamide peroxide, calcium bicarbonate peroxide, sodium bicarbonate peroxide and an oxygen radical releasing agent selected from the group consisting of ammonium persulfate and potassium persulfate; and (b) a secondary composition for use in a secondary phase of whitening.

35. A composition as described in claim 34, wherein said primary composition further comprises a buffer selected from the group consisting of urea, sodium carbonate, sodium bicarbonate, sodium hydroxide, potassium hydroxide, and calcium hydroxide, to maintain a basic pH.

36. A composition for use in whitening teeth then subjected to laser light comprising:

(a) a primary composition for use in a first phase of whitening; and (b) a secondary composition for use in a second phase of whitening comprising an oxygen radical generating agent selected from the peroxide group consisting of hydrogen peroxide, carbamide peroxide, calcium bicarbonate peroxide, sodium bicarbonate peroxide and an oxygen radical releasing agent selected from the group consisting of sodium carbonate, sodium bicarbonate, calcium carbonate, calcium hydroxide, and sodium perborate.

37. A composition as described in claim 36, wherein said secondary composition further comprises a buffer selected from the group consisting of urea, sodium carbonate, sodium bicarbonate, sodium hydroxide, potassium hydroxide, and calcium hydroxide, to maintain a basic pH.

* * * * *